(12) United States Patent
Smith et al.

(10) Patent No.: US 10,792,047 B2
(45) Date of Patent: Oct. 6, 2020

(54) SURGICAL CLOSURE DEVICES INCLUDING A STAPLING MEMBER

(71) Applicant: Boston Scientific Scimed, Inc., Maple Grove, MN (US)

(72) Inventors: Paul Smith, Smithfield, RI (US); Laura E. Christakis, Framingham, MA (US); John B. Golden, Norton, MA (US); Samuel Raybin, Marlborough, MA (US); Priya Khanchandani, Marlborough, MA (US); Naroun Suon, Lawrence, MA (US); Sean P. Fleury, Minneapolis, MN (US); Dylan Murphy, Walpole, MA (US); Liam Rolle, Roseau (DM); Bernard B. Schwartz, East Dorset, VT (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 94 days.

(21) Appl. No.: 16/143,186

(22) Filed: Sep. 26, 2018

(65) Prior Publication Data
US 2019/0021739 A1 Jan. 24, 2019

Related U.S. Application Data

(62) Division of application No. 14/946,217, filed on Nov. 19, 2015, now Pat. No. 10,111,672.
(Continued)

(51) Int. Cl.
*A61B 17/128* (2006.01)
*A61B 17/122* (2006.01)
(Continued)

(52) U.S. Cl.
CPC ........ *A61B 17/1285* (2013.01); *A61B 17/068* (2013.01); *A61B 17/0644* (2013.01);
(Continued)

(58) Field of Classification Search
CPC ............ A61B 17/1286; A61B 17/0644; A61B 17/068; A61B 17/1203; A61B 17/122
(Continued)

(56) References Cited

U.S. PATENT DOCUMENTS 5,499,990 A * 3/1996 Schulken ........... A61B 17/0469
606/103
7,169,157 B2 * 1/2007 Kayan ................ A61B 17/0644
140/123.6

(Continued)

*Primary Examiner* — Nathaniel C Chukwurah
(74) *Attorney, Agent, or Firm* — Fay Kaplun & Marcin, LLP

(57) ABSTRACT

This disclosure provides design, material, manufacturing method, and use alternatives for medical devices. An example medical device may include a medical device for delivery of a surgical closure member. The medical device includes an elongate tubular member having a proximal end, a distal end and a lumen extending therein. The elongate tubular member is adapted to be delivered through the working channel of an endoscope and the lumen is adapted to receive a surgical closure member. The medical device also includes a tissue support extending from the distal end of the elongate tubular member. The tissue support includes a support surface and the support surface is adapted to support tissue as a surgical closure member engages the tissue thereon.

19 Claims, 19 Drawing Sheets

Related U.S. Application Data

(60) Provisional application No. 62/083,700, filed on Nov. 24, 2014.

(51) Int. Cl.
| | | |
|---|---|---|
| *A61B 17/12* | (2006.01) | |
| *A61B 17/064* | (2006.01) | |
| *A61B 17/068* | (2006.01) | |
| *A61B 17/00* | (2006.01) | |
| *A61B 90/00* | (2016.01) | |

(52) U.S. Cl.
CPC ...... *A61B 17/122* (2013.01); *A61B 17/12013* (2013.01); *A61B 2017/0034* (2013.01); *A61B 2017/00867* (2013.01); *A61B 2017/0645* (2013.01); *A61B 2017/0649* (2013.01); *A61B 2090/037* (2016.02); *A61B 2090/0807* (2016.02); *A61B 2090/3966* (2016.02)

(58) Field of Classification Search
USPC .................................................. 227/175.1
See application file for complete search history.

(56) References Cited

U.S. PATENT DOCUMENTS

| | | | |
|---|---|---|---|
| 7,666,194 B2* | 2/2010 | Field | A61B 17/0469 606/144 |
| 2012/0101521 A1* | 4/2012 | Facchini De Souza | A61B 17/0644 606/223 |
| 2014/0257339 A1* | 9/2014 | Levy | A61B 17/068 606/139 |
| 2016/0157703 A1* | 6/2016 | Brooks | A61B 1/00094 600/104 |

* cited by examiner

US 10,792,047 B2

SURGICAL CLOSURE DEVICES INCLUDING A STAPLING MEMBER

PRIORITY CLAIM

The present application is a Divisional of U.S. patent applications Ser. No. 14/946,217 filed on Nov. 19, 2015, now U.S. Pat. No. 10,111,672 which claims priority to U.S. Provisional Application Ser. No. 62/083,700 filed on Nov. 24, 2014. The disclosure of the above patent(s)/application(s) is incorporated herein by reference.

TECHNICAL FIELD

The present disclosure generally relates to medical devices, and methods for manufacturing medical devices. More particularly, the present disclosure relates to surgical closure devices including a stapling member.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods.

BRIEF SUMMARY

This disclosure provides design, material, manufacturing method, and use alternatives for medical devices. An example medical device may include a medical device for delivery of a surgical closure member. The medical device includes an elongate tubular member having a proximal end, a distal end and a lumen extending therein. The elongate tubular member is adapted to be delivered through the working channel of an endoscope and the lumen is adapted to receive a surgical closure member. The medical device also includes a tissue support extending from the distal end of the elongate tubular member. The tissue support includes a support surface and the support surface is adapted to support tissue as a surgical closure member engages the tissue thereon.

Alternatively or additionally to any of the embodiments above, the tissue support includes an aperture configured to permit a surgical closure member to extend therethrough.

Alternatively or additionally to any of the embodiments above, the tissue support includes a first support member and a second support member extending away from the elongate tubular member, wherein the first support member is separated from the second support member, and wherein the aperture is defined between the first and second support members.

Alternatively or additionally to any of the embodiments above, the first and the second support members are substantially parallel.

Alternatively or additionally to any of the embodiments above, the first and the second support members includes a first support region, a second support region and a circular region, wherein the circular region is disposed between the first support region and the second support region, and wherein the first support region is substantially parallel to the second support region.

Alternatively or additionally to any of the embodiments above, at least a portion of the first and second support members are configured to be retracted into the elongate tubular member.

Alternatively or additionally to any of the embodiments above, the first and the second support members have a first configuration and a second configuration, and wherein the first and the second support members are retracted into the elongate tubular member in the first configuration, and wherein the first and the second support members extend away from and curl back toward the elongate tubular member in the second configuration.

Alternatively or additionally to any of the embodiments above, the first and the second support members include a shape memory material.

Alternatively or additionally to any of the embodiments above, the tissue support has a first configuration and a second configuration, wherein the tissue support is fully extended from the distal end of the elongate tubular member in the second configuration, and at least a portion of the tissue support is retracted within the elongate tubular member in the first configuration.

Alternatively or additionally to any of the embodiments above, the tissue support includes a distal end, and wherein the distal end of the tissue support is positionable distal of a surgical closure member deployed from the lumen of the elongate tubular member.

Alternatively or additionally to any of the embodiments above, the support surface is configured to be positioned between two or more layers of tissue.

Alternatively or additionally to any of the embodiments above, further comprising a surgical closure member adapted to be disposed within a portion of the lumen, and wherein the surgical closure member is configured to extend along the tissue support member.

Alternatively or additionally to any of the embodiments above, further comprising a plurality of interconnected surgical closure members, wherein a first portion of a first surgical closure member is designed to interconnect with the second portion of a second closure member.

Alternatively or additionally to any of the embodiments above, wherein each surgical closure member of the plurality of surgical closure members has a first configuration and a second configuration, wherein the first configuration is substantially straight and the second configuration is substantially circular, and wherein a single surgical closure member of the plurality of surgical closure members is adapted to separate from a remainder of the plurality of surgical closure members upon shifting from the first configuration to the second configuration.

Alternatively or additionally to any of the embodiments above, further comprising an orientation indicator, wherein the orientation indicator is disposed on a distal region of the elongate tubular member, and wherein a surgical closure member is designed to extend out from the elongate tubular member in a first radial plane, wherein the orientation indicator is designed to indicate the orientation of the first radial plane.

Alternatively or additionally to any of the embodiments above, the orientation indicator includes a visual indication portion.

A system for closing a surgical wound may include an elongate tubular member having a proximal end, a distal end and a lumen extending therein. The elongate tubular member is adapted to be delivered through the working channel of an endoscope, and the lumen is adapted to receive a stapling member. The system also includes one or more stapling members adapted to be disposed within the lumen of the elongate tubular member and the one or more stapling members are configured to extend from the distal end of the elongate tubular member. The system also includes a tissue support extending from the distal end of the elongate tubular member and the tissue support includes at least one support surface. The support surface includes an aperture configured to permit the one or more stapling members to extend therethrough.

Alternatively or additionally to any of the embodiments above, wherein the one or more stapling members includes a plurality of interlocked stapling members, and wherein a first stapling member of the plurality of interlocked stapling members is configured to separate from a second stapling member of the plurality of stapling members.

Alternatively or additionally to any of the embodiments above, wherein each stapling member of the plurality of stapling members has a first configuration and a second configuration, wherein the first configuration is substantially straight and the second configuration is substantially circular, and wherein a single stapling member of the plurality of stapling members is adapted to separate from a remainder of the plurality of stapling members upon shifting from the first configuration to the second configuration.

An example method of closing a surgical wound includes advancing a surgical closure device to a wound site. The surgical closure device includes an elongate tubular member having a distal end and a lumen extending therein, a surgical closure member configured to extend within the elongate tubular member and a tissue support having a support surface extending from the distal end of the elongate tubular member. The method also includes positioning the tissue support along one or more sections of tissue, wherein the support surface is configured to contact the one or more sections of tissue. The method also includes advancing the surgical closure member out of the elongate tubular member and engaging the surgical closure member with the one or more sections of tissue such that the surgical closure member couples the one or more tissue sections together.

An example medical device may include a medical device for delivery of a surgical closure member. The medical device includes an elongate tubular member having a lumen extending therethough. The elongate tubular member is adapted to be delivered through the working channel of an endoscope. The medical device also includes a stapling member adapted to extend through the elongate tubular member. The stapling member has a first frangible region and the stapling member is configured to sever at the first frangible region such that a distal region of the stapling member forms a first clip.

Alternatively or additionally to any of the embodiments above, the actuator is coupled to the elongate tubular member, the stapling member and/or a severing member, wherein the stapling member is configured to sever at the first frangible region upon manipulation of the actuator such that a distal region of the stapling member forms the first clip.

Alternatively or additionally to any of the embodiments above, the actuator includes a trigger mechanism, and wherein the trigger mechanism provides an audible, visual and/or tactile indication corresponding to severing the stapling member at the first frangible region.

Alternatively or additionally to any of the embodiments above, further comprising a deployment indicator, wherein the deployment indicator is designed to indicate when the first frangible region has been severed from the stapling member, and wherein the deployment indicator includes an audible indication, a visual indication and/or a tactile indication corresponding to the severing of the first frangible region from the stapling member.

Alternatively or additionally to any of the embodiments above, the stapling member includes a second frangible region, and wherein manipulation of the actuator is designed to incrementally sever the second frangible region after severing the first frangible region.

Alternatively or additionally to any of the embodiments above, the actuator is designed to provide an audible indication and/or a tactile indication corresponding to incrementally severing the second frangible region from the stapling member after severing the first frangible region from the stapling member.

Alternatively or additionally to any of the embodiments above, the stapling member is designed to shift between a constrained configuration and an unconstrained configuration.

Alternatively or additionally to any of the embodiments above, the constrained configuration of the stapling member is substantially straight and the unconstrained configuration of the stapling member includes a curve.

Alternatively or additionally to any of the embodiments above, the stapling member further comprises a second frangible segment of the stapling member, wherein the first frangible segment of the stapling member forms a first curve after being severed from the stapling member, and wherein the second frangible segment forms a second curve after being severed from the stapling member.

Alternatively or additionally to any of the embodiments above, further comprising an orientation indicator, wherein the orientation indicator is disposed on a distal region of the elongate tubular member, and wherein the stapling member is designed to extend out from and curve back toward the elongate tubular member in a first radial plane, wherein the orientation indicator is designed to indicate the orientation of the first radial plane.

Alternatively or additionally to any of the embodiments above, the orientation indicator includes a visual indication portion, and wherein the visual indication portion includes a radiopaque material.

Alternatively or additionally to any of the embodiments above, the visual indication portion includes a channel, and wherein the channel is designed to guide the stapling member parallel to the first radial plane.

Alternatively or additionally to any of the embodiments above, the first clip includes a proximal region and a distal locking region designed to engage with the proximal region.

Alternatively or additionally to any of the embodiments above, in manipulation of the actuator is designed to engage the proximal region with the distal locking region of the first clip before severing the stapling member at the first frangible region.

Another example medical device for closing a wound is disclosed. The medical device includes an elongate tubular member having a lumen extending therethough. The elongate tubular member is adapted to be delivered through the working channel of an endoscope. The medical device also includes a stapling member adapted to extend through the elongate tubular member. The stapling member has a first frangible region and the first frangible region has a first break portion and a first clip portion. The medical device also includes a severing member adapted to extend through the elongate tubular member and a first actuator movably coupled to the stapling member. Manipulation of the first actuator is adapted to advance the stapling member out of the elongate tubular member. The medical device also includes a second actuator moveably coupled to the severing member and the first clip portion is configured to sever at the first break region upon advancement of the severing member.

Alternatively or additionally to any of the embodiments above, the stapling member further comprises a second frangible region, wherein the second frangible region has a second break point and a second clip portion, and wherein manipulation of the first and second actuators incrementally severs the second clip portion at the second break portion after severing the first clip portion at the first break portion.

Alternatively or additionally to any of the embodiments above, the first frangible segment of the stapling member forms a first curve after being severed from the stapling member, and wherein the second frangible segment forms a second curve after being severed from the stapling member.

Alternatively or additionally to any of the embodiments above, further comprising an orientation indicator, wherein the orientation indicator is disposed on a distal region of the elongate tubular member, and wherein the stapling member is designed to extend out from and curve back toward the elongate tubular member in a first radial plane, and wherein the orientation indicator is designed to indicate the orientation of the first radial plane.

A method of closing a surgical wound is disclosed. The method includes delivering a surgical closure clip to a wound site with a medical device. The medical device includes an elongate tubular member having a lumen extending therethough. The elongate tubular member is designed to be delivered through the working channel of an endoscope. The medical device also includes a stapling member designed to extend through the elongate tubular member and the stapling member has a first frangible region. The method also includes advancing the first frangible region into and/or through tissue and severing the stapling member at the first frangible region such that a distal region of the stapling member forms a first clip retained in the tissue.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
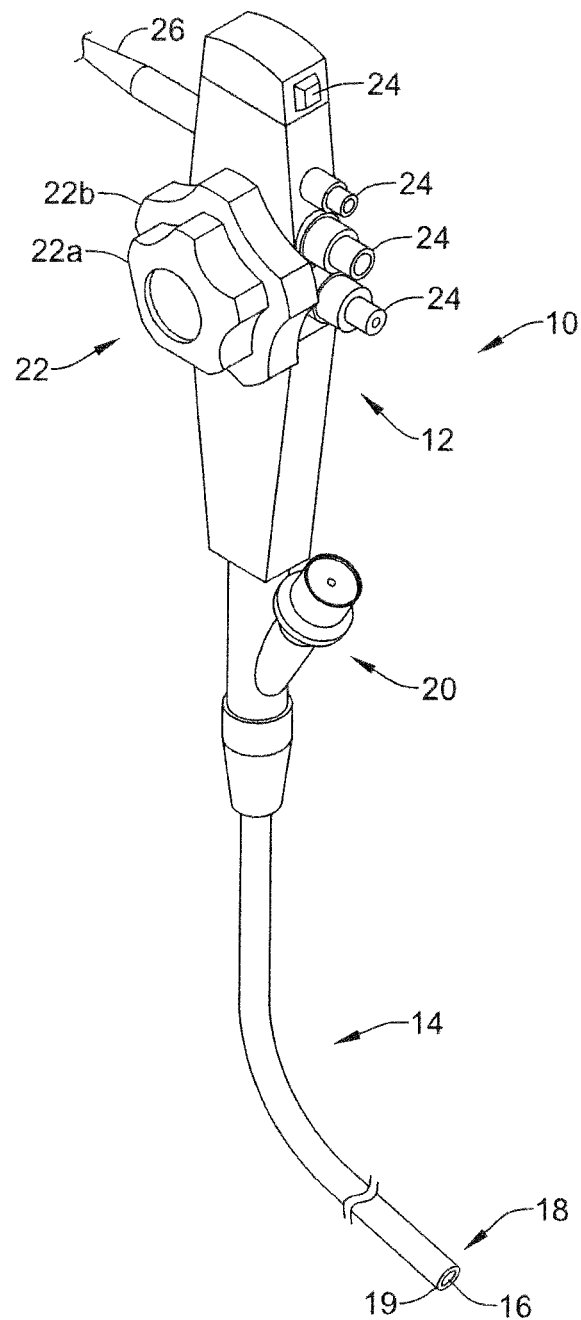
FIG. 1 is a perspective view of an endoscope assembly.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DETAILED DESCRIPTION

The following detailed description should be read with reference to the drawings in which similar elements in different drawings are numbered the same. The drawings, which are not necessarily to scale, depict illustrative embodiments and are not intended to limit the scope of the disclosure.

An example endoscope and/or endoscope assembly 10 is illustrated in FIG. 1. Endoscope 10 may be any of a number of types of endoscopes or related medical devices usually identified by the particular anatomy desired to be reached. For example, endoscope 10 may be a bronchoscope, colonoscope, duodenoscope, esophagoscope, guidetubes, introducers (without or without vision or visualization capabilities), or any other type of endoscope or related medical device. The endoscope 10 may include a handpiece 12 and an elongate shaft 14 extending distally from the handpiece 12 to a distal tip 18. The elongate shaft 14 may include a lumen defining a working channel 16 extending through the elongate shaft 14 from a distal end 19 near the distal tip 18 of the shaft 14 to an access port 20 that may be positioned in the handpiece 12 or another portion of the endoscope 10. Although the endoscope 10 is depicted with a single working channel in FIG. 1, it can be appreciated that in other embodiments, the endoscope 10 may include multiple working channels.

The handpiece 12 may include one or more controls 22, such as rotating knobs, which may be used to control movement of the distal tip 18 of the shaft 14 during operation. For example, a first rotating knob 22a may control up and down movement or deflection of the distal tip 18 of the shaft 14, while a second rotating knob 22b may control side-to-side movement or deflection of the distal tip 18 of the shaft 14. The handpiece 12 may also include one or more buttons 24, which may be used to activate suction or deliver fluid such as air, saline and/or water, etc. through a lumen of the endoscope 10 or perform other functions as desired. Additionally, the handpiece 12 may include an optical cable 26 connected to an external light source (not shown). Other configurations may be implemented.

Figure 2:
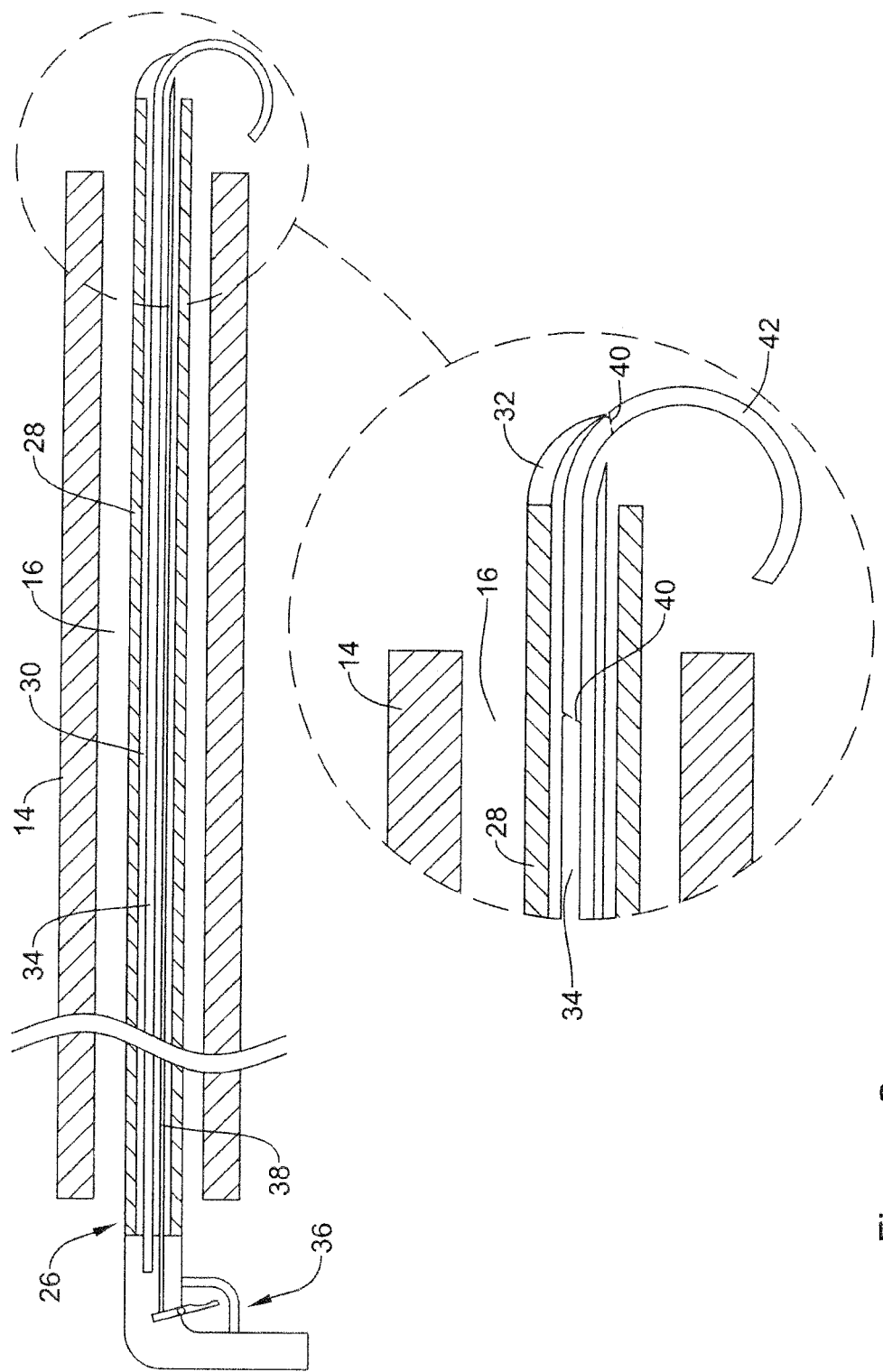
FIG. 2 is a partial cross-sectional side view of an example endoscopic instrument.

The endoscope 10 may be used in a number of medical procedures. For example, FIG. 2 illustrates an example endoscopic instrument 26 that may be used with the endoscope 10. In at least some instances, the endoscopic instrument 26 may be used to close a surgical wound, close an opening, etc. This may include the use of staples, surgical closure members, clips, sutures, etc. Some additional details regarding the use of the endoscopic instrument 26 arc disclosed herein.

The endoscopic instrument 26 may include a tubular member 28 having a lumen 30 defined therein. The tubular member 28 may be designed to fit within the working channel 16 of the endoscope 10. A staple orienting member 32 may be disposed at the distal end of the tubular member 28. The staple orienting member 32 may have a curved orientation that has some resemblance to a curved beak that overlies at least a portion of the distal end of the tubular member 28. This may help direct the staple member 34 in the desired direction. In at least some instances, the staple orienting member 32 may include a visual indicator (e.g., a color, pattern, or the like). In some of these and/or other instances, the staple orienting member 32 may include a radiopaque marker or the like.

A staple member and/or surgical closure member 34 may be disposed within the lumen 30. It is understood that the term staple member and surgical closure member may he used interchangeably throughout the following disclosure. In at least some instances, the staple member 34 is an elongate tubular member formed from a single monolith of material. In other words, rather than being a collection of staples secured together in a magazine or clip, the staple member 34 is a single piece that may be severed or otherwise broken apart to form a plurality of individual staples. When in use, a user may sever the staple member 34 into a plurality of individual staples "on demand." In other words, the staple member 34 can serve as a template that can provide the desired number of individual staples whenever needed during an intervention. This may be desirable for a number of reasons. For example, a user would not need to determine how many individual staples to load for a given intervention. Instead, a single staple member 34 can be utilized to provide just one staple or to provide a plurality of staples. Furthermore, because all of the individual staples are part of a unified singular member arranged in a linear manner, the use of the staple member 34 may allow for the profile of the endoscopic instrument to be relatively smaller.

In some instances, the surgical closure member 34 may include individual staples disposed within the lumen 30. Further, as discussed in greater detail below, the individual surgical closure members 34 may be interconnected with one another in a head-to-tail configuration. For example, the head of one surgical closure member may interconnect with the tail of an adjacent surgical closure member. When in use, the interconnected surgical closure members 34 may be advanced and/or retracted from the lumen 30 as a single, interconnected member. Upon exiting the lumen 30, the individual surgical members 34 may separate from the single, interconnected member.

In some instances, the staple member 34 may be formed form a shape memory material that is designed to shift between a first (e.g., substantially linear) configuration and a second (e.g., curved) configuration. For example, when the staple member 34 is disposed within the tubular member 28 (e.g., constrained within the tubular member 28), the staple member 34 may be held in a substantially linear configuration. When urged out from the distal end of the tubular member 28, the staple member 34 may shift to the curved orientation. Engaging the staple member 34 with the staple orienting member 32 may aid in the shifting to the curved configuration. Alternatively, when the staple member 34 is not formed from a shape memory material, the staple orienting member 32 may actively shift the staple member 34 to a curved configuration.

A handle 36 is coupled to the proximal end of the tubular member 28. The handle 36 may include a variety of structural features. For example, the handle 36 may include one or more actuation mechanisms that are designed to advance and/or manipulate the staple member 34 distally within the tubular member 28. In at least some instances, the actuation mechanism includes a trigger assembly. The trigger assembly may include a ratchet or suitable mechanism that engages the proximal end region of the staple member 34 so as to distally advance the staple member 34 within the tubular member 28. Advancing the staple member 34 may occur in incremental steps of a fixed distance, in steps of variable distances, or the like, or in a non-stepwise manner. The trigger mechanism is one example. Other actuation mechanisms are contemplated. For example, in some instances other actuation mechanisms such as a rotational actuator may be used in conjunction with or instead of the trigger mechanism.

In addition, the actuation mechanism may include, for example, an actuating or severing wire 38. The severing wire 38 may be designed to break apart the staple member 34 at frangible regions 40. For example, the staple orienting member 32 may have a curved orientation that bends down along the distal end of the tubular member 28. When the staple member 34 is urged distally, the staple member 34 may contact the staple orienting member 32 and cause a distal region 42 to bend. In some instances, the distal region 42 may bend into a loop.

After distally advancing the staple member 34, the severing wire 38 may be actuated. This may include bringing the end of the severing wire 38 into contact with the frangible region 40. Because the staple member 34 may be squeezed or pinched between the severing wire 38 and the staple orienting member 32, the severing wire 38 may break off a portion (e.g., distal region 42) of the staple member 34.

Figure 3:
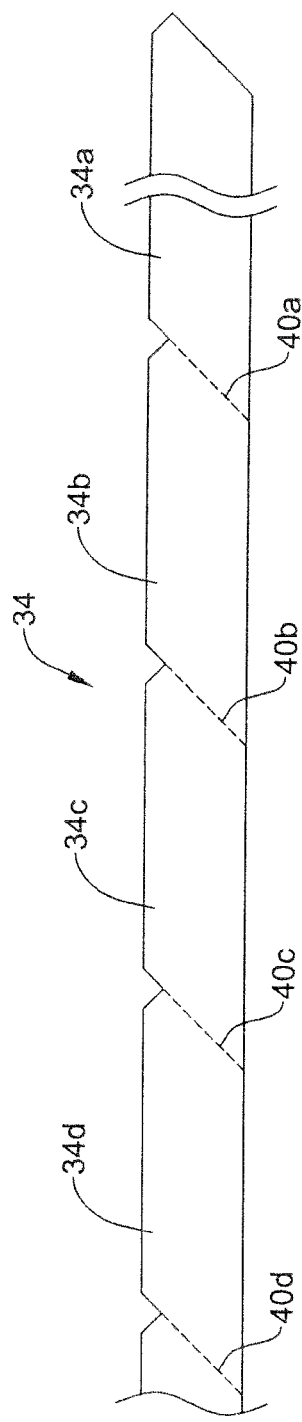
FIG. 3 is a side view of an example stapling member.
Figure 4:
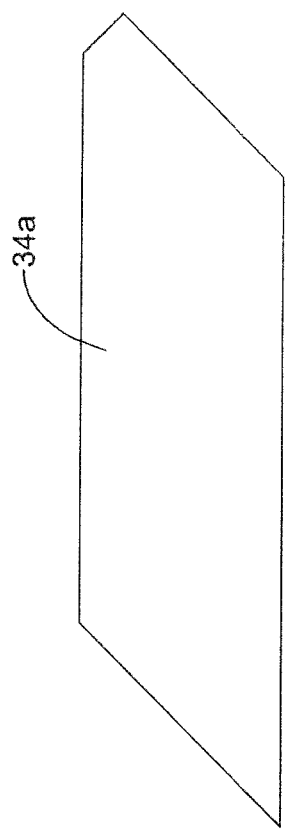
FIG. 4 is a side view of an example clip.

FIG. 3 is a side view of the staple member 34. Here it can be seen that the staple member 34 may include a plurality of frangible regions 40a-d. In this example, four frangible regions 40a-d are shown. In other implementations, the number of frangible regions may vary. Severing the staple member 34 at one of the frangible regions (e.g., frangible region 40a) may break off a section 34a of the staple member 34 that may define a staple or clip as shown in FIG. 4.

In at least some instances, the frangible regions 40a-d may be oriented at an angle. By doing so, when the staple member 34 is broken at one of the frangible regions 40a-d, the angled orientation of frangible regions 40a-d results in the served region (e.g., region 34a) and the remaining portions of the staple member 34 (e.g., including region 34b) may have an angled and/or "sharpened" orientation. This may aid the passing of the staple member 34 into target tissue.

Figure 5:
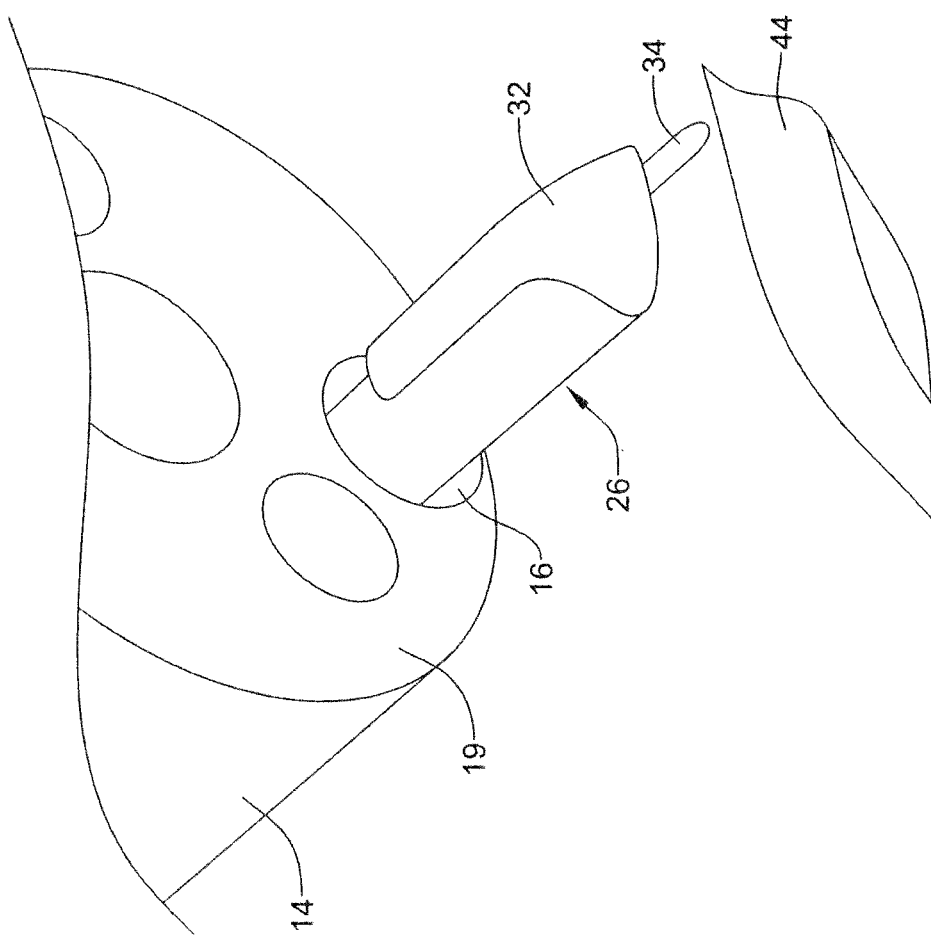
FIGS. 5-8 illustrate an example method for closing a surgical wound.
Figure 6:
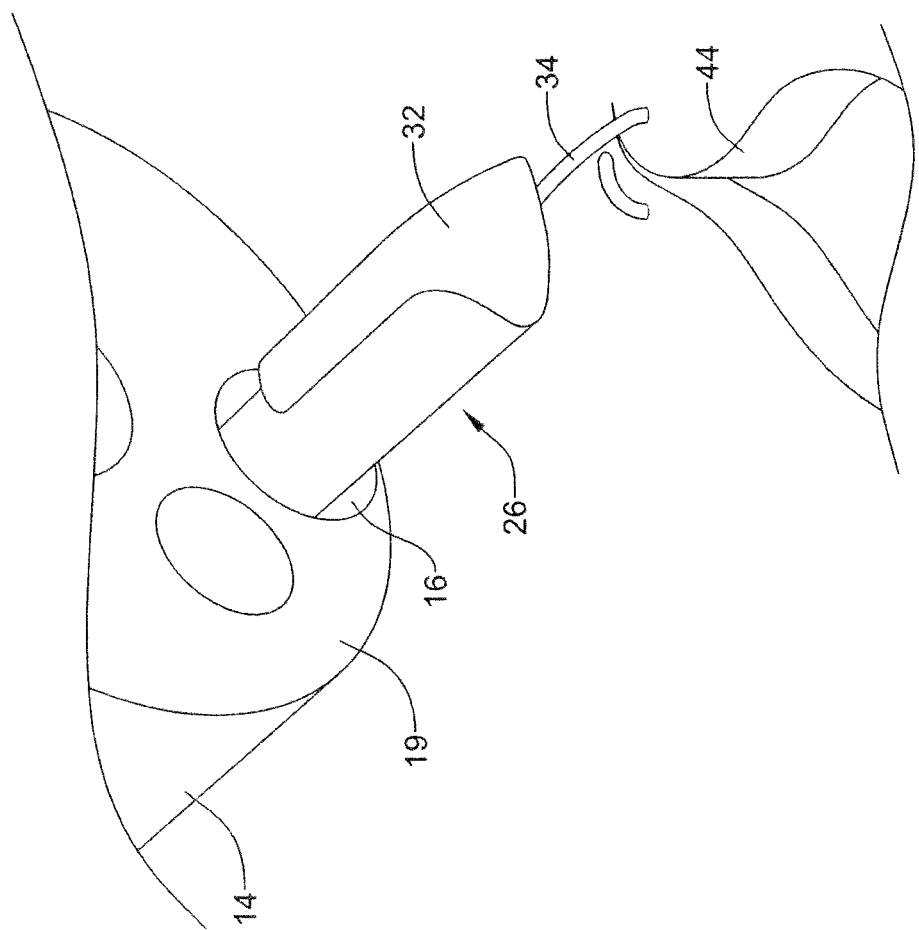

FIGS. 5-8 illustrate an example method for closing a surgical wound 44. The method may include distally advancing the staple member 34 within the endoscopic instrument 26. This may include bringing the staple member 34 into contact with the staple orienting member 32 as shown in FIG. 5. As indicated herein, the staple member 34 may include a shape memory material such that advancing the staple member 34 out from the endoscopic instrument 26 may allow the staple member 34 to take a curved shape or orientation. In some of these and in other instances, bringing the staple member 34 into contact with the staple orienting member 32 may cause or aid the curving of the staple member 34 as shown in FIG. 6. Either way, the staple orienting member 32 may direct the staple member 34 into contact with the surgical wound 44 and loop the staple member 34 through the surgical wound 44.

Figure 7:
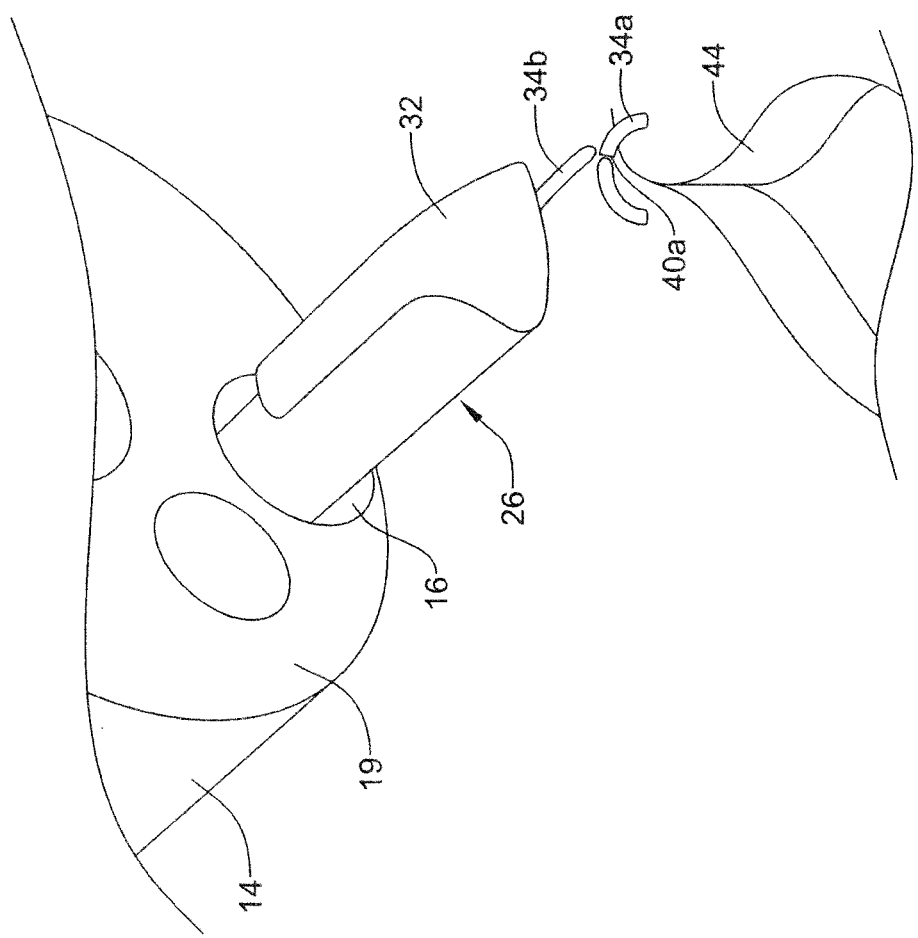
Figure 8:
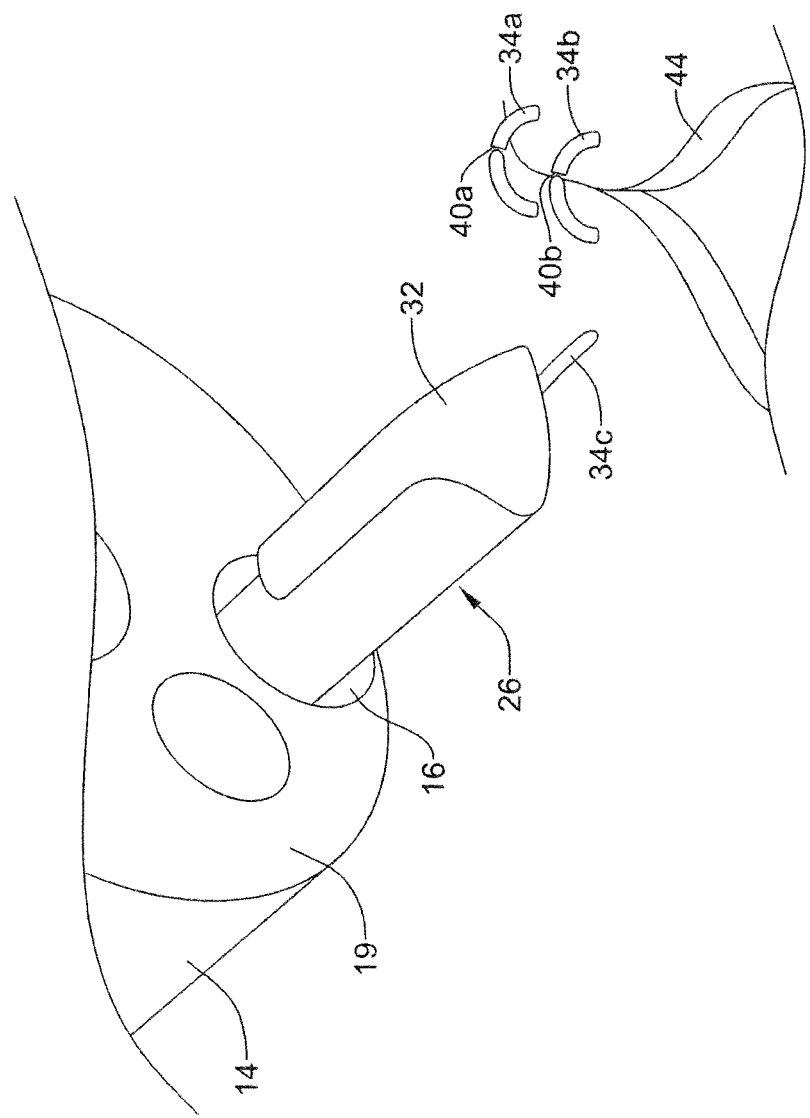

The actuation mechanism may be utilized to break the staple member 34 at the frangible region 40a so that the staple 34a separates from the remainder of the staple member 34b as shown in FIG. 7. In doing so, the surgical wound 44 may begin to close. In some instances, a single staple (e.g., staple 34a) may suitably close the wound 44. In other instances, the process may be repeated (e.g., incrementally repeated) one or more times to place additional staples. For example, the actuation mechanism may be utilized to break the remainder of staple member at the frangible region 40b so that a second clip 34b separates from the remainder of the staple member 34c as shown in FIG. 8. In some instances, an anchoring member, a suture, or both (not shown) may be used to join or otherwise secure together a plurality of individual staples (e.g., staples 34a, 34b, etc.). When using the anchoring member/suture, individual staples may be "laced up" or otherwise brought together to more securely close the wound 44.

Figure 9:
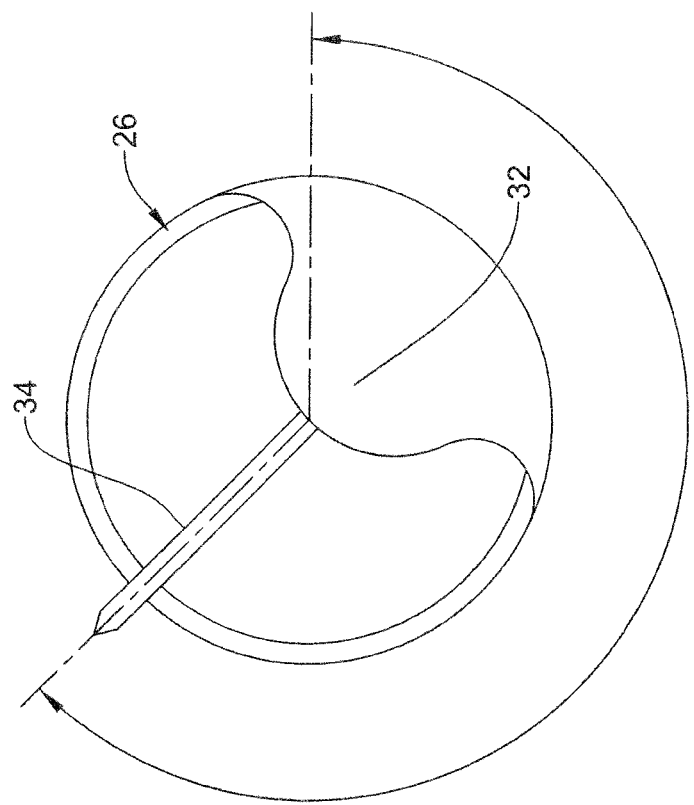
FIG. 9 is an end view of a portion of an example endoscopic instrument.
Figure 9:
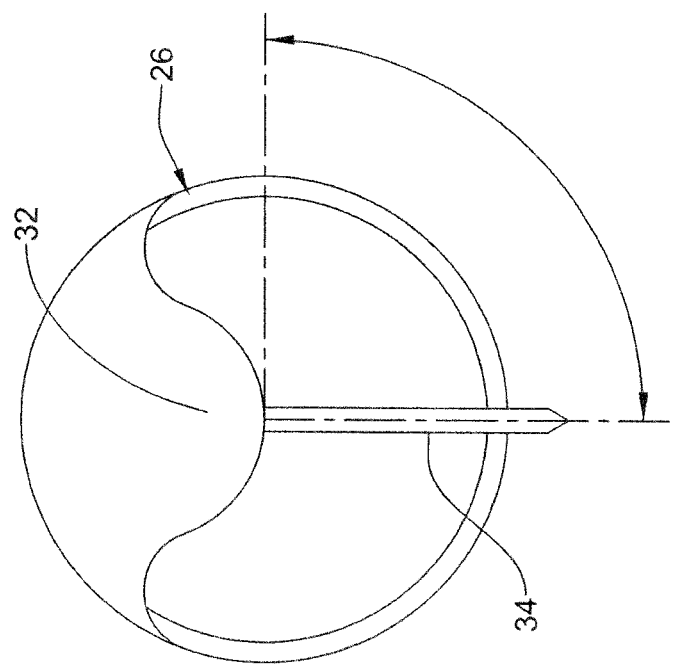

In some instances, the circumferential orientation of the staple orienting member 32 may be used to guide the staple member 34. For example, FIG. 9 illustrates that the staple orienting member 32 may be rotated to orient the staple member 34 in the desired direction/orientation. Rotating the staple orienting member 32 may include rotating the endoscopic instrument 26. In some of these and in other instances, the staple orienting member 32 may be rotatable about the endoscopic instrument 26 using a steering mechanism or suitable rotatable member. Because the staple orienting member 32 overlies a portion of the distal end of the endoscopic instrument 26, the direction that the staple member 34 may emerge from the endoscopic instrument 26 may be controlled by the orientation of the staple orienting member 32.

Figure 10:
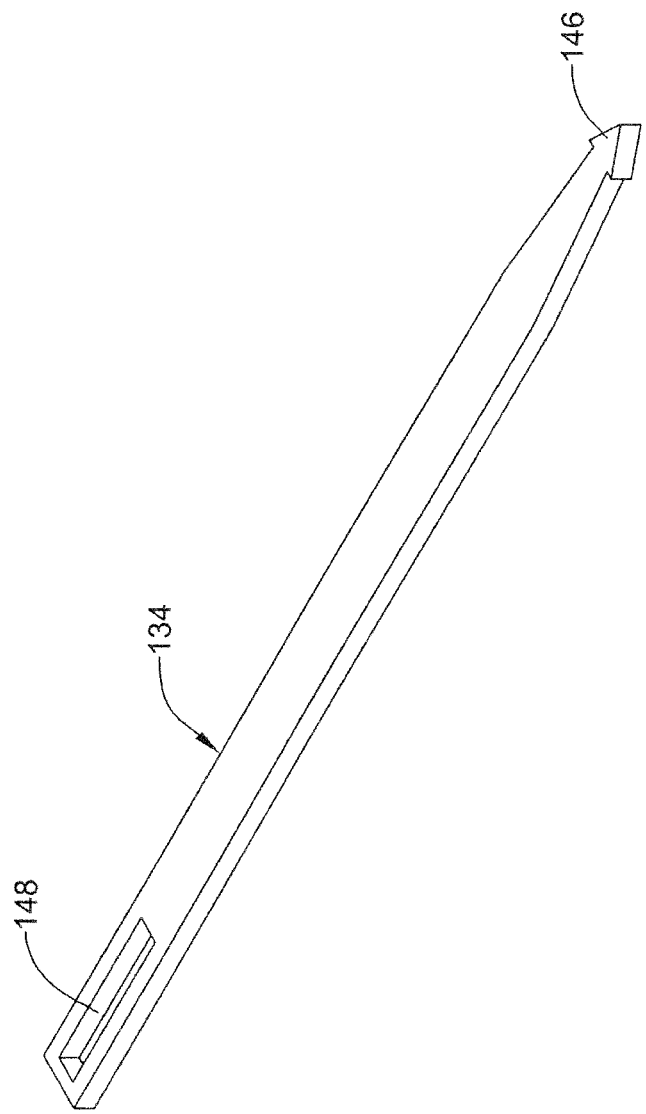
FIG. 10 is a perspective view of an example clip in a first configuration.
Figure 11:
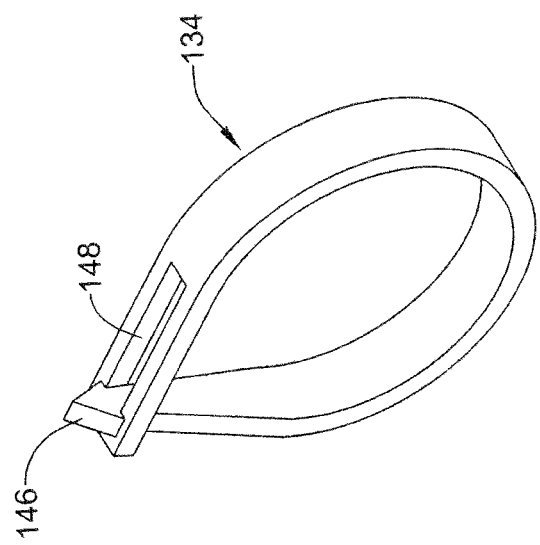
FIG. 11 is a perspective view of an example clip in a second configuration.

The staple member 34 and/or other staple members disclosed herein may include one or more structural features that allow the staple member 34 to take a looped configuration and "lock" in the looped configuration. This "locking feature" may include a variety of structural components that are formed in the staple member 34 and that can be utilized after separating the staple member 34 into individual staples. Some examples of the locking features that are contemplated are disclosed herein. For example, FIG. 10 illustrates another example the staple member 134 that may be similar in form and function to other staple members disclosed herein. The staple member 134 may include a first end region 146 and a second end region 148. In this example, the staple member 134 may be formed into a loop configuration so that the first end region 146 is brought into contact with the second end region 148 as shown in FIG. 11. More particularly, the first end region 146 may have an enlarged end that can be passed through the second end region 148 and become mechanically interlocked. The precise shapes and orientation of end regions 146 and 148 can vary from what is shown. In some instances, regions 146 and 148 may be brought together using the actuation mechanism. In other instances, another structure such as a suture may be used to bring together ends 146 and 148 and secure the staple member 134 in the loop configuration.

Figure 12:
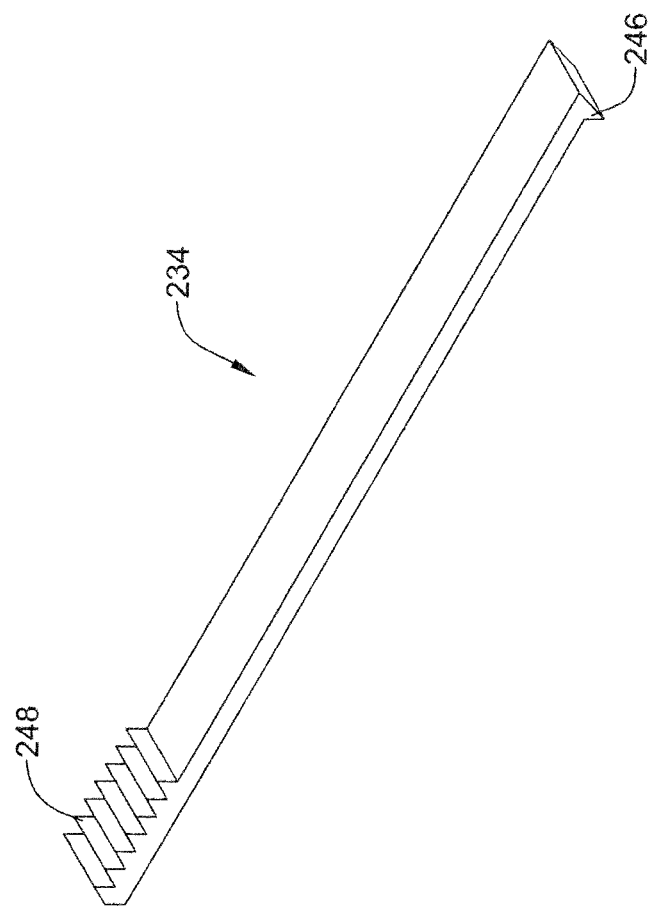
FIG. 12 is a perspective view of an example clip in a first configuration.
Figure 13:
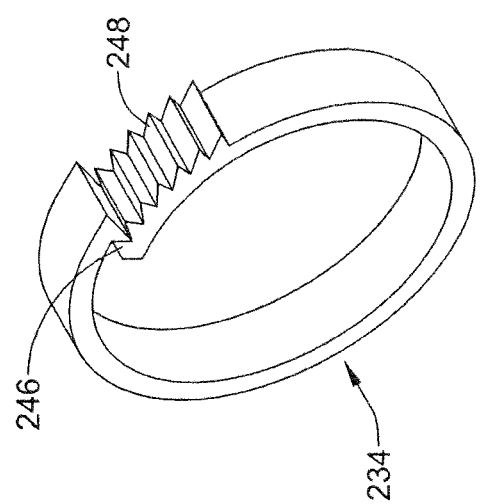
FIG. 13 is a perspective view of an example clip in a second configuration.

FIG. 12 illustrates another example staple member 234 that may be similar in form and function to other staple members disclosed herein. The staple member 234 may include a first end region 246 and a second end region 248. In this example, the first end region 246 may include a projection that is designed to engage a series of corresponding ridges formed along the second end region 248. Thus, when the staple member 234 is formed into a loop, the projection formed on the first end region 246 may engage the ridges along the second end region 248 as shown in FIG. 13.

Figure 14:
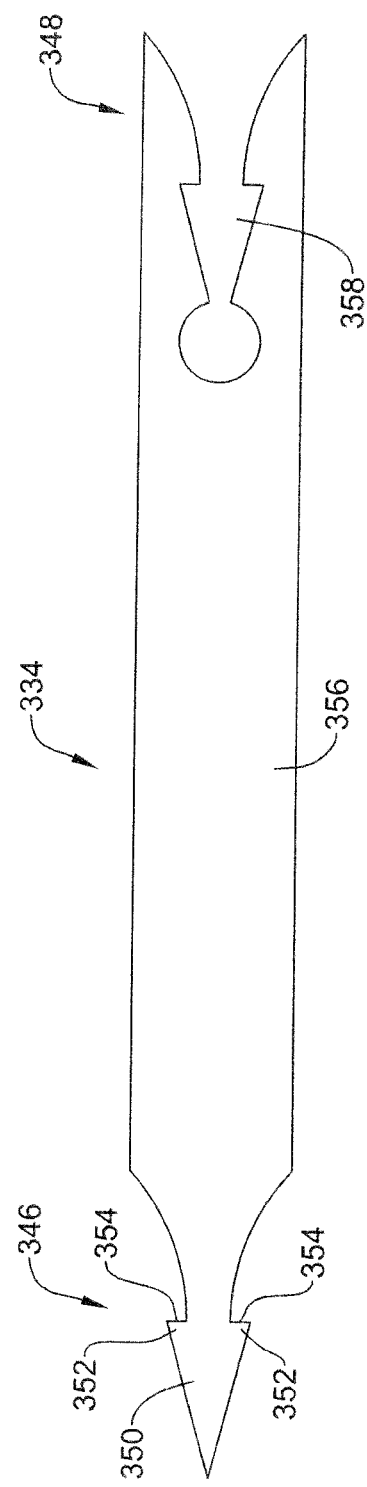
FIG. 14 is a top view of an example stapling member.

FIG. 14 illustrates another example staple member 334 that may be similar in form and function to other staple members disclosed herein. The staple member 334 may include a first end region 346 (e.g., leading end region) and a second end region 348 (e.g., trailing end region). In this example, the first end region 346 may include an enlarged portion 350 that may be configured to engage, pierce and/or penetrate tissue. The enlarged portion 350 may have one or more barb-like projections 352 defining a shoulder surface 354. In use, the shoulder surface 354 may act to prevent the enlarged portion 350 from disengaging or retracting back through tissue pierced by the enlarged portion 350. In other words, the enlarged portion 350 may resemble an arrowhead, having a sharp projection and barb-like projections designed to pierce and remain engaged with tissue during a surgical wound closure procedure.

As depicted in FIG. 14, staple member 334 may include a second end region 348 positioned away from the first end region 346. A body region 356 may be disposed between the first end region 346 and the second end region 348. The relationship of the first end region 346 and the second end region 348 may be described as a "head-to-tail" configuration, whereby the first end region 346 may be considered the "head" and the second end region the "tail." The second end region 348 may include a cutout and/or aperture 358 configured to receive and/or interconnect with the first end region 346. Further, the cutaway shape of an aperture 358 may be substantially similar (e.g., complementary in shape, size and/or configuration) to the profile of the first end region 346.

Figure 15:
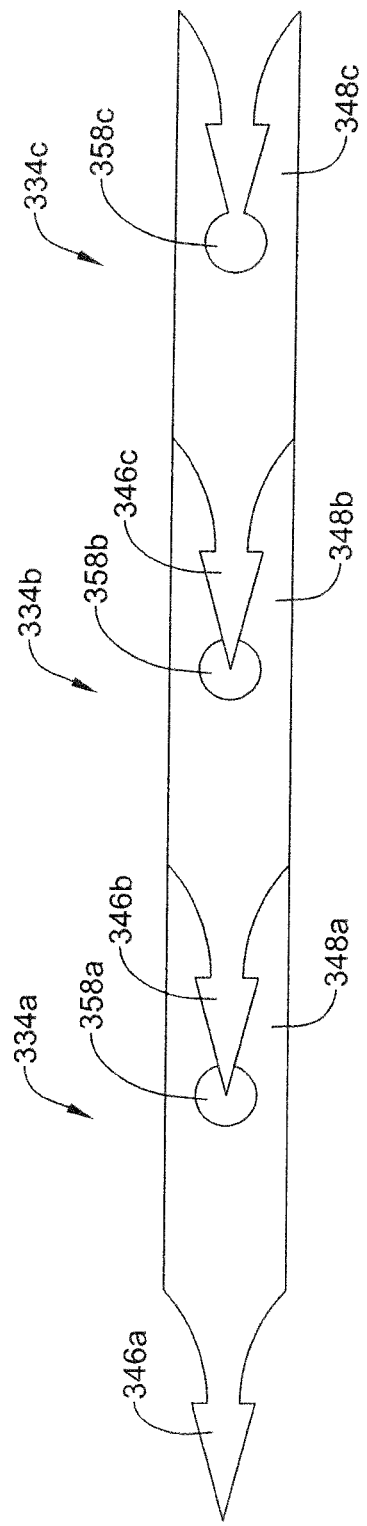
FIG. 15 is a top view of an example plurality of stapling members.

FIG. 15 illustrates a plurality of staple members 334a-334c interconnected in a "head-to-tail" manner. In other words, the tail of each staple member may receive and/or interconnect with the head of an adjacent staple member. As shown in FIG. 15, second end regions 348a and 348b of the staple members 334a and 334b (including apertures 358a and 358b), may receive and/or interconnect with first end regions 346b and 346c of the staple members 334b and 334c, respectively. It is contemplated that the plurality of staple members may include 2, 3, 4, 5, 6, 7, 8, 9, 10, 15, 20, 30, 50, 75, 100 or greater interconnected staple members.

As stated above, a plurality of staple members may be advanced through the lumen 30 as a single, interconnected member. In some instances, upon exiting the lumen 30, individual staple members may separate from the plurality of interconnected staple members. Further, a single staple member may have a first configuration in which the staple member is substantially straight and a second configuration in which the staple is substantially circular or arcuate. When disposed with lumen 30 (either as a single member or part of a plurality of members), the staple member may be substantially straight. Upon exiting the lumen, however, the staple member may assume a circular or arcuate shape. It can be appreciated that as an individual staple member takes on a circular or arcuate shape as it exits and extends away from lumen 30, the radial inward force generated from forming a circular or arcuate shape may cause the staple member to disconnect from the plurality of staple members.

Figure 16:
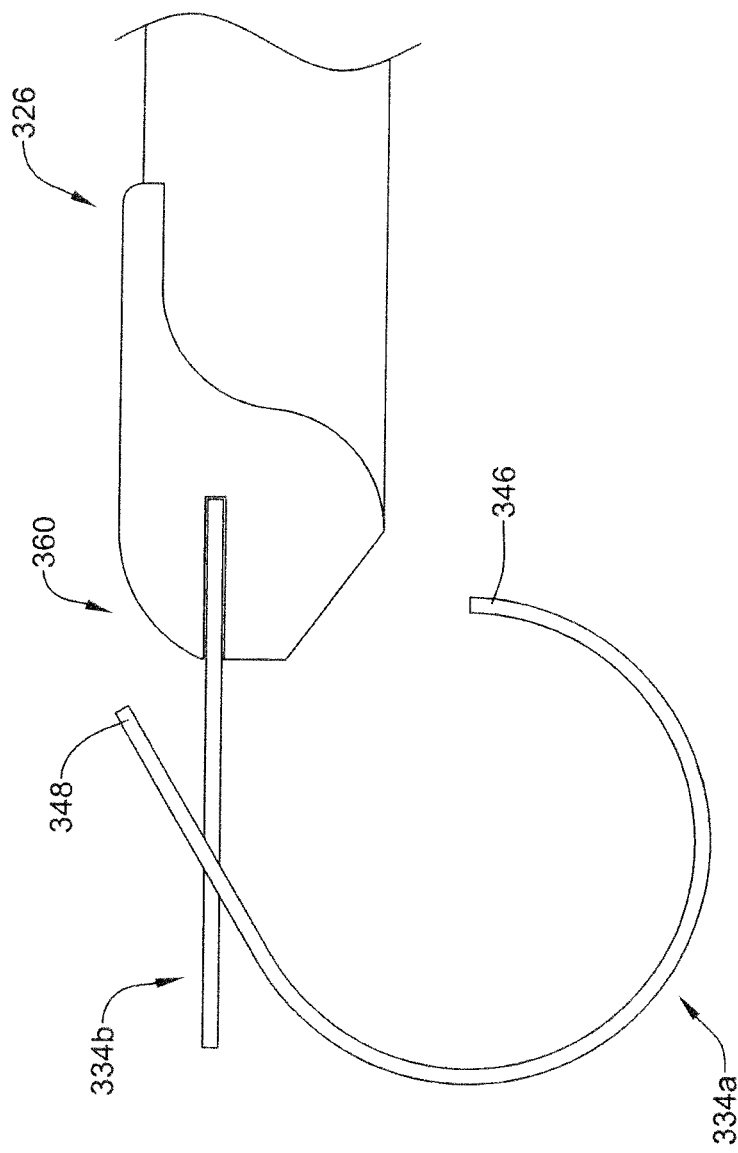
FIG. 16 is a side view of an example stapling member disconnecting from a plurality of stapling members.

FIG. 16 illustrates a single staple member 334a in a circular or arcuate shape after exiting and extending away from a distal end 360 of an endoscopic instrument 326. As illustrated, a single staple member 334b may remain in contact with the endoscopic instrument 326. Further, while remaining in contact with the endoscopic instrument 326, single staple member 334b may remain in a substantially straight configuration. However, as shown, the single staple member 334a may assume a substantially circular or arcuate configuration and disconnect from the single staple member 334b. In some instances, the staple members (either singular or as a plurality) may include a superelastic material, for example a superelastic alloy such as nitinol. The staple members may be configured to automatically revert to an equilibrium or unstressed circular or arcuate configuration from a biased or stressed substantially straight configuration (e.g., constrained into a straightened state within the lumen of the endoscopic instrument 326) upon exiting the lumen of the endoscopic instrument 326. It is contemplated that in some instances, the staple members (either singular or as a plurality) may include a shape memory material, such as a shape memory alloy or a shape memory polymer. The shape memory material may allow the staple members to automatically shift from a first (e.g. straight) to a second (e.g. circular) configuration.

Figure 17:
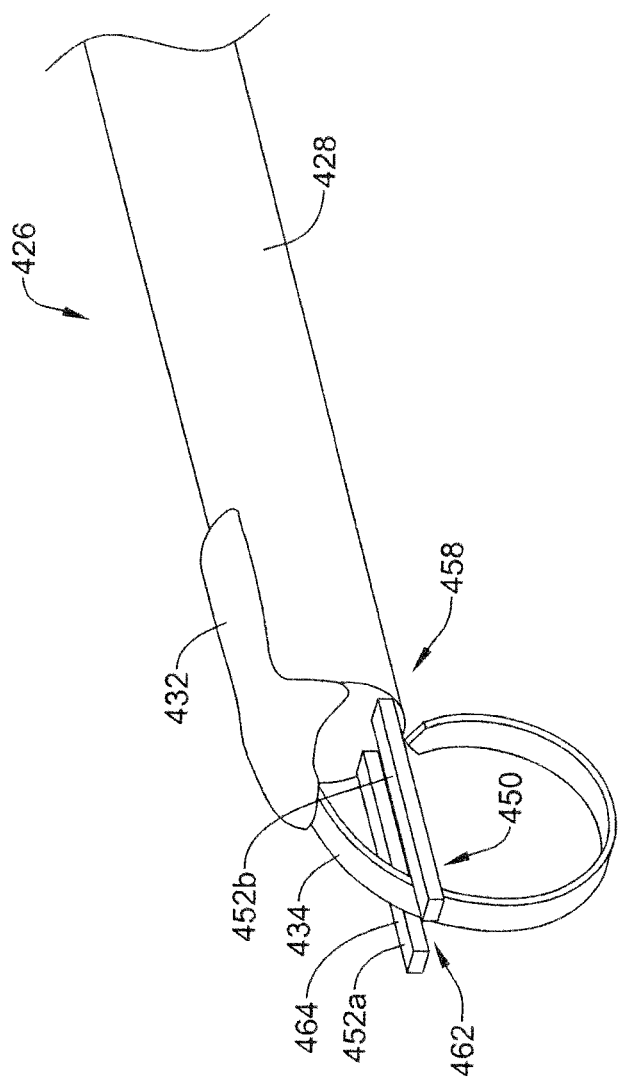
FIG. 17 is a perspective view of an example endoscopic instrument having a tissue support.

FIG. 17 illustrates another example endoscopic instrument 426 including a tissue support 450 extending from a distal end 458 of a tubular member 428. In some instances, the tissue support 450 may include a first tissue support member 452a and a second tissue support member 452b. Further, the tissue support members 452a and 452b may be substantially parallel to each other. However, while not shown in the figures, it is contemplated that in some instances the tissue support 450 may include a single, unitary member extending from a distal end 458 of the tubular member 428. In use, the tissue support 450 may provide a rigid platform to support one or more sections of tissue during a surgical wound closure procedure.

An aperture 462 may exist between the tissue support members 452a and 452b. A surgical closure member 434 may extend between the tissue support members 452a and 452b and into and/or through the aperture 462. While FIG. 17 depicts the tissue support 450 including the aperture 462 positioned between the first tissue support member 452a and the second tissue support member 452b, it is contemplated that the tissue support 450 may include a single unitary member having the aperture 462 disposed therein. For example, the tissue support 450 may include a unitary member having an aperture 462 resembling a hole in the center of the unitary member. Further, the surgical closure member 434 may extend into and through the aperture 462 located in a unitary member.

In some instances, the tissue support 450 may be rigidly fixed relative to the tubular member 428. For example, the tissue support 450 may extend away from the distal end 458 of the tubular member 428 and resemble a solid platform upon which one or more tissue sections may be positioned. In other instances, the tissue support 450 may retract into the tubular member 428. For example, the endoscopic instrument 426 may include an actuator (not shown) coupled to the tissue support 450. The actuator may manipulate the tissue support 450 from a first position in which the tissue support 450 is disposed within the endoscopic instrument 426 to a second position in which the tissue support 450 is extended outside (e.g., distally beyond the distal tip) of the endoscopic instrument 426.

Similar to that stated above, the endoscopic instrument 426 may include a circumferential orienting member 432. In some instances, the circumferential orientation of the staple orienting member 432 may be used to guide the staple member 434. For example, the orienting member 432 may be rotated to orient the staple member 434 in the desired direction/orientation. Rotating the staple orienting member 432 may include rotating the endoscopic instrument 426.

Additionally, as shown in FIG. 17, the orienting member 432 may be used to guide the staple member 434 between the tissue support members 452a and 452b and into thee aperture 462 between the tissue support members 452a and 452b.

As shown in FIG. 17, the stapling member 434 may extend along the tissue support 450 when moving from a first straightened position to a second circular position. In other words, the tissue support members 452a and 452b may define a planar region in which the staple member 434 may be positioned when moving from a first straightened position to a second circular position. In some instances, each of the tissue support members 452a and 452b may include a top surface 464. The top surface 464 may be orthogonal to the planar region (described above) in which the staple member 434 may be positioned. Additionally, in some instances a distal end of the tissue support 450 may extend distally beyond a distal end of the staple member 434.

Figure 18:
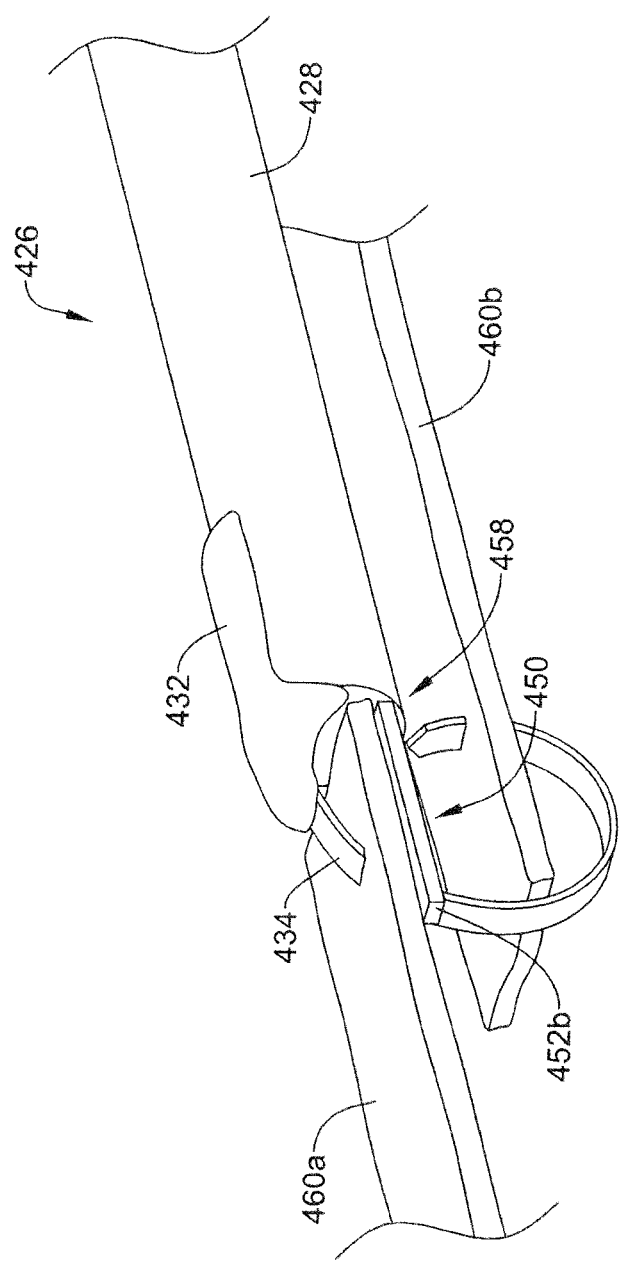
FIG. 18 is a perspective view of the example endoscopic instrument of FIG. 17 positioned adjacent tissue sections.

In use, one or more sections of tissue may be positioned on the top surface 464 of the tissue support 450 prior to being engaged with the staple member 434. FIG. 18 illustrates an example method for closing a surgical wound utilizing the example tissue closure device described in FIG. 17. The example method may utilize either a rigid tissue support 450 or a tissue support 450 that has been extending out of the distal end 458 of the endoscopic instrument 426. In either instance, the tissue support 450 may be placed between adjacent tissue sections 460a and 460b. As shown in FIG. 18, the tissue support 450 may provide a platform substantially parallel to the position of the tissue sections 460a and 460b. This configuration may provide support for the tissue as the stapling member 434 is advanced out of the tubular member 428 and engages the topmost tissue section 460a. After piercing the tissue section 460a, the stapling member 434 may be further advanced to pierce the tissue section 460b. As shown in FIG. 18, the circular configuration of the tissue member 434 may allow the stapling member 434 to engage and/or wrap around one or more tissue sections. Additionally, the radial "tightening" of the staple member 434 may allow the staple member 434 to couple and/or draw the tissue sections 460a and 460b together. After the stapling member 434 has been fully released from the tubular member 428, the endoscopic instrument 426 may be positioned adjacent to the inserted staple in order to continue closing the wound.

Figure 19:
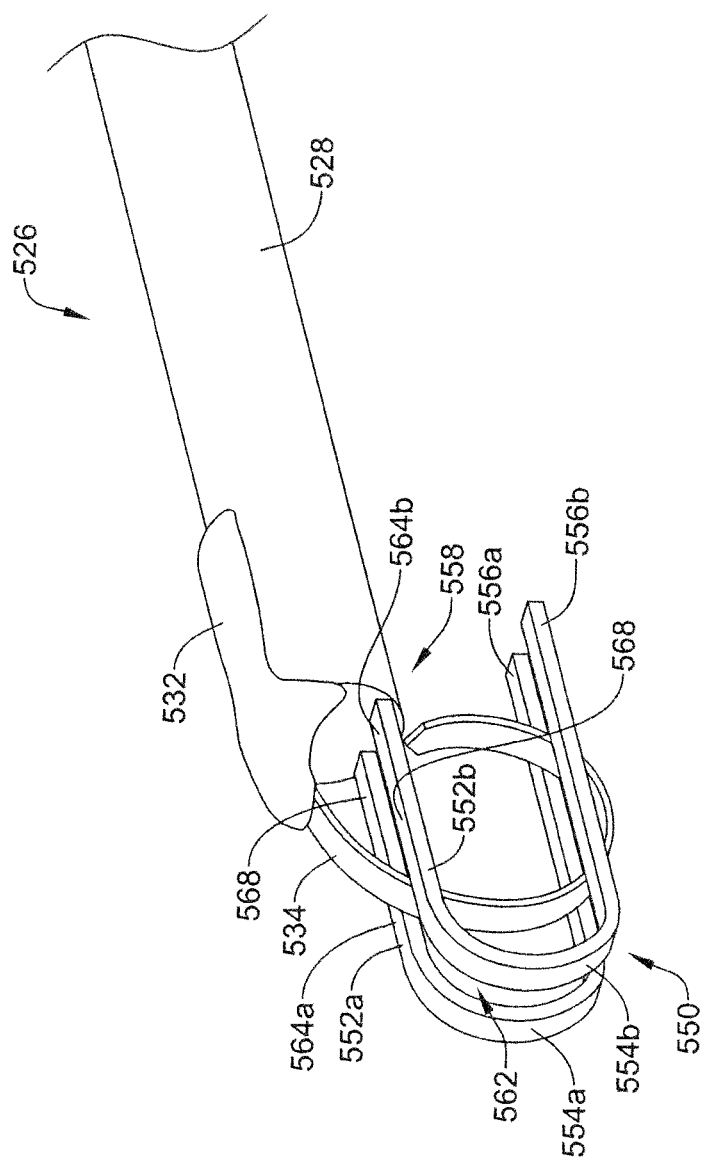
FIG. 19 is a perspective view of an example endoscopic instrument having a tissue support.

FIG. 19 illustrates another example endoscopic instrument 526 including a tissue support 550 extending from a distal end 558 of a tubular member 528. In some instances, the tissue support 550 may include a first tissue support member 552a and a second tissue support member 552b. The tissue support members 552a and 552b may be parallel to each other. As shown in FIG. 19, the tissue support member 552a may include a distally extending region 564a, a curved region 554a, and a proximally extending region 556a. Similarly, tissue support 552b may include a distally extending region 564b, a curved region 554b, and a proximally extending region 556b. In other words, the general shape of each of tissue support members 552a and 552b may resemble that of the end of a paper clip such that it extends away from the distal end 558, curls back toward the tubular member 528 and extends back toward the tubular member 528. As depicted, the distally extending regions 564a, 564b may be parallel to the proximally extending regions 556a, 556b. Further, the proximally extending regions 556a and 556b may extend below the bottom surface of the tubular member 528.

An aperture 562 may exist between the tissue support members 552a and 552b. A surgical closure member 534 may extend between the tissue support members 552a, 552b and into the aperture 562. While FIG. 19 depicts the tissue support 550 including the aperture 562 positioned between the first tissue support member 552a and the second tissue support member 552b, it is contemplated that the tissue support 550 may include a single unitary member having the aperture 562 disposed therein. For example, the tissue support 550 may include a unitary member having an aperture 562 resembling a hole in the center of the unitary member. Further, the surgical closure member 534 may extend into and through the aperture 562 located in a unitary member.

In some instances, the tissue support 550 may retract into the tubular member 528. For example, the endoscopic instrument 526 may include an actuator (not shown) coupled to the tissue support 550. The actuator may manipulate the tissue support 550 from a first position in which the tissue support 550 is disposed within the endoscopic instrument 526 to a second position in which the tissue support 550 is extended outside (e.g., distally beyond) the endoscopic instrument 526.

Similar to that stated above, the endoscopic instrument 526 may include a circumferential orienting member 532. In some instances, the circumferential orientation of the staple orienting member 532 may be used to guide the staple member 534. For example, the orienting member 532 may be rotated to orient the staple member 534 in the desired direction/orientation. Rotating the orienting member 532 may include rotating the endoscopic instrument 526. Additionally, as shown in FIG. 19, the orienting member 532 may be used to guide the staple member 534 between the tissue support members 552a, 552b and into the aperture 562.

As shown in FIG. 19, the stapling member 534 may extend along the tissue support 550 when moving from a first straightened position to a second circular position. Further, the stapling member 534 may extend along the distally extending regions 564a and 564b, the curved regions 554a and 554b, and the proximally extending regions 556a and 556b. In other words, the tissue support members 552a and 552b may define a planar region in which the staple member 534 may be positioned when moving from a first straightened position to a second circular position. In some instances, each of the tissue support members 552a and 552b may include a top surface 568. The top surface 568 may be orthogonal to the planar region (described above) in which the staple member 534 may be positioned. Additionally, in some instances a distal end of the tissue support 550 may extend distally beyond a distal end of the staple member 534.

Figure 20:
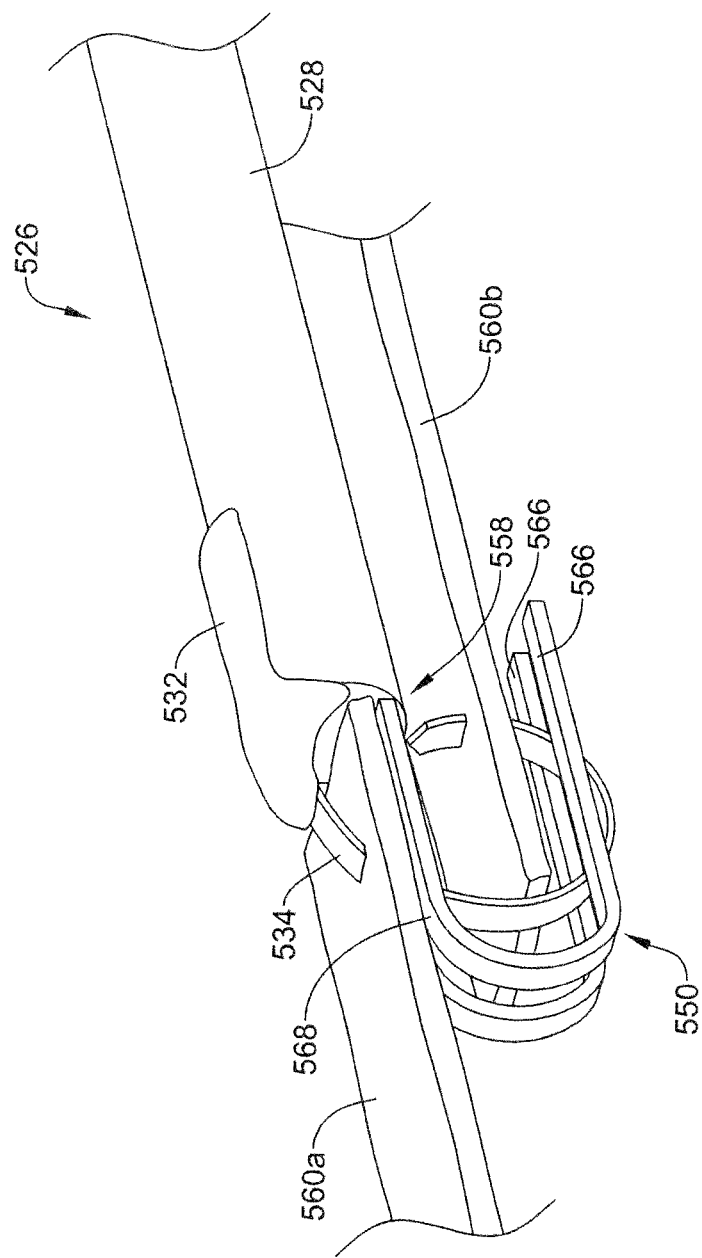
FIG. 20 is a perspective view of the example endoscopic instrument of FIG. 19 positioned adjacent tissue sections.

In use, one or more sections of tissue may be positioned on the top surface 568 of the tissue support members 552a and 552b prior to being engaged with the staple member 534. FIG. 20 illustrates an example method for closing a surgical wound utilizing the example tissue closure device described in FIG. 19. The example method may utilize either a rigid tissue support 550 or a tissue support 550 that has been extended out of the distal end 558 of the endoscopic instrument 526. In either instance, the tissue support 550 may be placed between the adjacent tissue sections 560a and 560b. Further, the tissue support 550 may wrap around one or more sections of tissue. In other words, the tissue section 560a may be positioned on the top surface 568, while the tissue section 560b may be sandwiched between the distally extending regions 552a, 552b and the proximally extending regions 556a, 556b.

As shown in FIG. 20, the tissue support 550 may provide one or more platforms substantially parallel to the tissue sections 560a and 560b. This configuration may provide support for the tissue as the stapling member 534 is advanced out of the tubular member 528 and engages the topmost tissue section 560a. After piercing the tissue section 560a, the stapling member 534 may be further advanced to pierce the tissue section 560b. The tissue section 560b may be supported by either the bottom side of the distally extending region 552a, 552b and/or top surface 566 of both proximally extending regions 556a, 556b.

As shown in FIG. 20, the circular configuration of the tissue support 550 may allow the stapling member 534 to engage and/or wrap around one or more tissue sections. Additionally, the radial "tightening" of the staple member 534 may allow the staple member 534 to couple and/or draw the tissue sections 560a and 560b together. After the stapling member 534 has been fully released from the tubular member 528, the tubular member 528 may move to a position adjacent to the previously inserted staple member and advance another staple.

Another example endoscopic closure device may include a tubular member configured to support and/or grasp one or more sections of tissue with a suction mechanism by sucking the tissue into a distal end region of the tubular member (e.g., drawing the tissue into a distal end region of the tubular member under vacuum) prior to engaging and/or placing a tissue closure member therein. The tubular member may be configured to suck and/or pull adjacent sections of tissue up into a lumen and/or cavity of the tubular member. For example, the tubular member may resemble the end of straw. As the sections of tissue are held within the tubular member (e.g. with suction), one or more stapling members may engage the sections of tissue. The distal end region of the tubular member may draw the tissue sections together inside the lumen and/or cavity of the tubular member. After coupling the tissue sections, the suction or vacuum may be turned off, thereby releasing the joined tissue. In some instances, the closure device may incorporate a grasping mechanism in lieu of the suction mechanism. In other instances, both the suction mechanism and a grasping mechanism may be utilized together.

The materials that can be used for the various components of assembly (and/or other assemblies disclosed herein) and the various tubular members disclosed herein may include those commonly associated with medical devices. For simplicity purposes, the following discussion makes reference to endoscopic instrument and other components of endoscope. However, this is not intended to limit the devices and methods described herein, as the discussion may be applied to other similar tubular members and/or components of tubular members or devices disclosed herein.

Endoscopic instrument and/or other components of assembly may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota). In some other embodiments, a superelastic alloy, for example a superelastic nitinol can he used to achieve desired properties.

In at least some embodiments, endoscopic instrument and/or other portions of assembly may also be doped with, made of, or otherwise include a radiopaque material. Radiopaque materials are understood to be materials capable of producing a relatively bright image on a fluoroscopy screen or another imaging technique during a medical procedure. This relatively bright image aids the user of assembly in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of assembly to achieve the same result.

In some embodiments, a degree of Magnetic Resonance Imaging (MRI) compatibility is imparted into assembly. For example, assembly and/or endoscopic instrument, or portions thereof, may be made of a material that does not substantially distort the image and create substantial artifacts (e.g., gaps in the image). Certain ferromagnetic materials, for example, may not be suitable because they may create artifacts in an MRI image. Assembly and/or endoscopic instrument, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed is:

1. A medical device for delivery of a surgical closure member, comprising:
an elongate tubular member having a lumen extending therethrough, wherein the elongate tubular member is adapted to be delivered through the working channel of an endoscope;
a stapling member adapted to extend through the elongate tubular member, wherein the stapling member has a first frangible region; and
wherein the stapling member is configured to sever at the first frangible region such that a distal region of the stapling member forms a first clip.

2. The medical device of claim 1, further comprising an actuator, wherein the actuator is coupled to the elongate tubular member, the stapling member and/or a severing member, wherein the stapling member is configured to sever at the first frangible region upon manipulation of the actuator such that a distal region of the stapling member forms the first clip.

3. The medical device of claim 2, wherein the actuator includes a trigger mechanism, and wherein the trigger mechanism provides an audible, visual and/or tactile indication corresponding to severing the stapling member at the first frangible region.

4. The medical device of claim 1, further comprising a deployment indicator, wherein the deployment indicator is designed to indicate when the first frangible region has been severed from the stapling member, and wherein the deployment indicator includes an audible indication, a visual indication and/or a tactile indication corresponding to the severing of the first frangible region from the stapling member.

5. The medical device, of claim 4, wherein the stapling member includes a second frangible region, and wherein manipulation of the actuator is designed to incrementally sever the second frangible region after severing the first frangible region.

6. The medical device of claim 5, wherein the actuator is designed to provide an audible indication and/or a tactile indication corresponding to incrementally severing the second frangible region from the stapling member after severing the first frangible region from the stapling member.

7. The medical device of claim 1, wherein the stapling member is designed to shift between a constrained configuration and an unconstrained configuration.

8. The medical device of claim 7, wherein the constrained configuration of the stapling member is substantially straight and the unconstrained configuration of the stapling member includes a curve.

9. The medical device of claim 1, wherein the stapling member farther comprises a second frangible segment of the stapling member, wherein the first frangible segment of the stapling member forms a first curve after being severed from the stapling member, and wherein the second frangible segment forms a second curve after being severed from the stapling member.

10. The medical device of claim 1, further comprising an orientation indicator, wherein the orientation indicator is disposed on a distal region of the elongate tubular member, and wherein the stapling member is designed to extend out from and curve back toward the elongate tubular member in a first radial plane, wherein the orientation indicator is designed to indicate the orientation of the first radial plane.

11. The medical device of claim 10, wherein the orientation indicator includes a visual indication portion, and wherein the visual indication portion includes a radiopaque material.

12. The medical device of claim 11, wherein the visual indication portion includes a channel, and wherein the channel is designed to guide the stapling member parallel to the first radial plane.

13. The medical device of claim 1, wherein the first clip includes a proximal region and a distal locking region designed to engage with the proximal region.

14. The medical device of claim 13, wherein in manipulation of the actuator is designed to engage the proximal region with the distal locking region of the first clip before severing the stapling member at the first frangible region.

15. A medical device for closing a wound, comprising:
an elongate tubular member having a lumen extending therethrough, wherein the elongate tubular member is adapted to be delivered through the working channel of an endoscope;
a stapling member adapted to extend through the elongate tubular member, wherein the stapling member has a first frangible region, and wherein the first frangible region has a first break portion and a first clip portion;
a severing member adapted to extend through the elongate tubular member;
a first actuator movably coupled to the stapling member, wherein manipulation of the first actuator is adapted to advance the stapling member out of the elongate tubular member; and
a second actuator moveably coupled to the severing member, wherein the first clip portion is configured to sever at the first break region upon advancement of the severing member.

16. The medical device of claim 15, wherein the stapling member further comprises a second frangible region, wherein the second frangible region has a second break point and a second clip portion, wherein manipulation of the first and second actuators incrementally severs the second clip portion at the second break portion after severing the first clip portion at the first break portion.

17. The medical device of claim 16, wherein the first frangible segment of the stapling member forms a first curve after being severed from the stapling member, and wherein the second frangible segment forms a second curve after being severed from the stapling member.

18. The medical device of claim 15, further comprising an orientation indicator, wherein the orientation indicator is disposed on a distal region of the elongate tubular member, and wherein the stapling member is designed to extend out from and curve back toward the elongate tubular member in a first radial plane, and wherein the orientation indicator is designed to indicate the orientation of the first radial plane.

19. A method of closing a surgical wound, the method comprising:
   delivering a surgical closure clip to a wound site with a medical device, wherein the medical device includes:
   an elongate tubular member having a lumen extending therethrough, wherein the elongate tubular member is designed to be delivered through the working channel of an endoscope, and
   a stapling member designed to extend through the elongate tubular member, wherein the stapling member has a first frangible region;
   advancing the first frangible region into and/or through tissue; and
   severing the stapling member at the first frangible region such that a distal region of the stapling member forms a first clip retained in the tissue.

* * * * *